(12) United States Patent
Toriumi

(10) Patent No.: US 9,095,674 B2
(45) Date of Patent: Aug. 4, 2015

(54) NOSE CLIP

(75) Inventor: Dean M. Toriumi, Riverside, IL (US)

(73) Assignee: Dean M. Toriumi, Riverside, IL (US)

( * ) Notice: Subject to any disclaimer, the term of this patent is extended or adjusted under 35 U.S.C. 154(b) by 570 days.

(21) Appl. No.: 12/538,388

(22) Filed: Aug. 10, 2009

(65) Prior Publication Data
US 2011/0034950 A1 Feb. 10, 2011

(51) Int. Cl.
*A61M 29/00* (2006.01)
*A61M 15/08* (2006.01)
*A61F 5/08* (2006.01)

(52) U.S. Cl.
CPC . *A61M 15/08* (2013.01); *A61F 5/08* (2013.01)

(58) Field of Classification Search
CPC ............... B42F 1/02; B42F 1/04; B42F 1/06; B42F 1/08; B42F 1/10; A61F 5/08; A61M 15/08
USPC ............. 606/199, 196, 204.45, 204.15, 20, 4; 128/848, 206.11, 203.22, 200.24, 128/204.12; 24/67, 67.9; 29/525.08
See application file for complete search history.

(56) References Cited

U.S. PATENT DOCUMENTS

| | | | | |
|---|---|---|---|---|
| 5,479,944 A | * | 1/1996 | Petruson | 128/858 |
| 5,922,006 A | * | 7/1999 | Sugerman | 606/204.45 |
| 6,004,342 A | * | 12/1999 | Filis | 606/199 |
| 6,238,411 B1 | * | 5/2001 | Thorner | 606/199 |
| 7,111,589 B1 | * | 9/2006 | Terwilliger et al. | 119/800 |
| 7,114,495 B2 | * | 10/2006 | Lockwood, Jr. | 128/200.24 |
| D554,752 S | * | 11/2007 | Reed | D24/135 |
| 7,390,331 B2 | * | 6/2008 | Santin et al. | 606/199 |
| 2002/0000227 A1 | * | 1/2002 | Duyke et al. | 128/200.24 |
| 2006/0100649 A1 | * | 5/2006 | Hart | 606/157 |
| 2006/0144084 A1 | * | 7/2006 | Verma | 63/12 |
| 2006/0207598 A1 | * | 9/2006 | Thomas | 128/206.11 |
| 2007/0221219 A1 | * | 9/2007 | Christy et al. | 128/203.16 |
| 2008/0184995 A1 | * | 8/2008 | Ierulli | 128/200.24 |
| 2009/0093840 A1 | * | 4/2009 | MacDonald | 606/199 |

FOREIGN PATENT DOCUMENTS

| CN | 2678610 Y | 2/2005 |
|---|---|---|
| JP | 2003/319807 A | 11/2003 |

OTHER PUBLICATIONS

PCT International Search Report and Written Opinion of the International Searching Authority, mailing date of Oct. 26, 2010, for PCT/US2010/044987 (6 pgs.).

* cited by examiner

*Primary Examiner* — Katherine Dowe
*Assistant Examiner* — Sidharth Kapoor
(74) *Attorney, Agent, or Firm* — Brinks Gilson & Lione

(57) ABSTRACT

A nose clip includes an outer support member adapted to contact an outside surface of a nose. A bridge connected at a first end to the outer support member; and an inner support member connected to a second end of the bridge and adapted to be inserted into the nostril and to contact an inner surface of the nostril. When inserted, tension generated between the outer support member and the inner support member causes lateral movement of a surface within the nostril and opens a nasal airway. Additionally, the inner support can be curved to create an outward movement of the lateral wall of the nose. This in turn enables improved breathing.

22 Claims, 8 Drawing Sheets

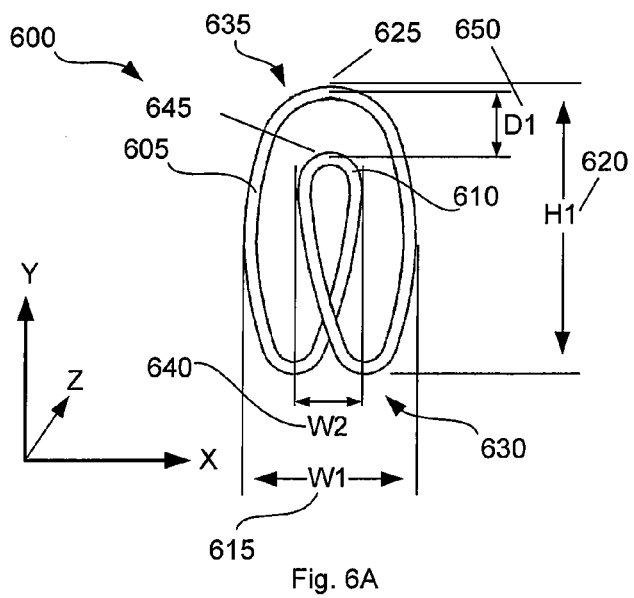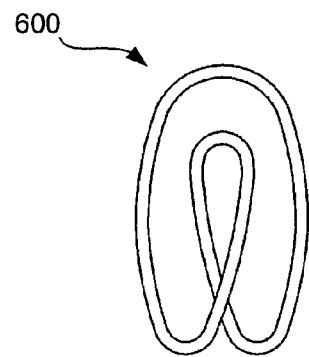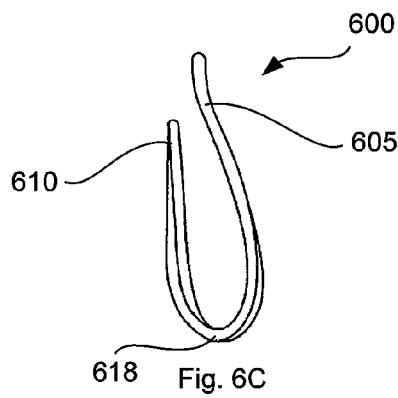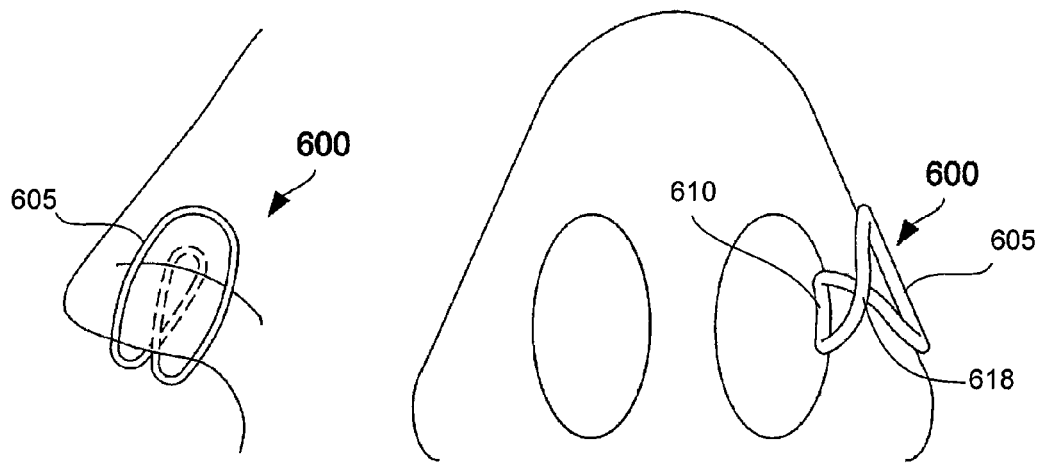
Fig. 6A    Fig. 6B    Fig. 6C    Fig. 6D    Fig. 6E

NOSE CLIP

BACKGROUND

1. Field of Application

The present application is related to medical devices. More specifically, the present application is related to an apparatus for opening the nasal airway.

2. Discussion

Many individuals experience difficulty breathing due to collapse within the nasal cavity. It is estimated that as much as 50% of the population over the age of 50 experience some form of nasal collapse. This can result in varying degrees of discomfort, difficulty breathing, and sleepless nights. In some cases, if left untreated, nasal collapse can result in apnea and hypoxia, which can be harmful to one's health.

Some individuals resort to expensive surgery of the nasal cavity to alleviate problems associated with nasal collapse. During the surgery, the cartilage around the nasal passage may be restructured to improve airflow through the nasal passage. Other individuals resort to homemade solutions to find relief. For example, some individuals insert objects, such as paper clips, within the nasal cavity to open the nasal passageway. However, this can be dangerous because the inserted object can become lodged in the airway.

Products, such as Breathe Right® nasal strips, may provide relief in some cases. These products are usually strips of malleable material with an adhesive on one side. The user bends the strip over the outside of the nose. The adhesive then bonds the clip to the nose and tension within the clip pulls the outside of the nose in a lateral direction. However, there are several problems with these products. First, many users develop irritation and allergic reactions to the adhesive used on these products, thus preventing further use of the products. Second, because the product is mounted on the outside of the nose, the amount of lateral displacement provided inside the nasal cavity depends on the nasal anatomy and characteristics of the nasal sidewall. Other devices that are placed into the airway are designed to push on the medial wall of the nose (septum) to open the airway. This can cause irritation on the septum and even erosion of the nasal mucosa.

BRIEF DESCRIPTION OF THE DRAWINGS

FIGS. 6A and 6B are front and back views, respectively, of an alternative embodiment of the nose clip;

FIG. 6C is a side view of the nose clip shown in FIG. 6A;

FIG. 6D is a side view illustration of the nose clip of FIG. 6A in an attached configuration;

FIG. 6E is a bottom view illustration of the nose clip of FIG. 6A in an attached configuration;

DETAILED DESCRIPTION

Embodiments below generally describe a nose clip that improves airflow in the nasal airway by applying outward pressure against an interior surface of the nasal cavity. The outward pressure causes the nasal valve in the nose to open. This in turn improves airflow in the nasal airway.

The nose clip may be used to help those who suffer from nasal collapse to breathe more freely. Adhesives, which may cause irritation or allergic reactions, are not required to achieve this effect, although they may be utilized.

In addition to those suffering from nasal collapse, the nose clip may be used by those who would simply like to breathe more freely in general. For example, athletes or exercise enthusiasts may use the nose clip to improve breathing during periods of high physical exertion to provide maximal nasal airflow.

Other embodiments provide a drug-delivery apparatus that clips to the nose. Generally, the drugs are delivered into the nasal airway when air is drawn through the nasal airway.

Figure 1A:
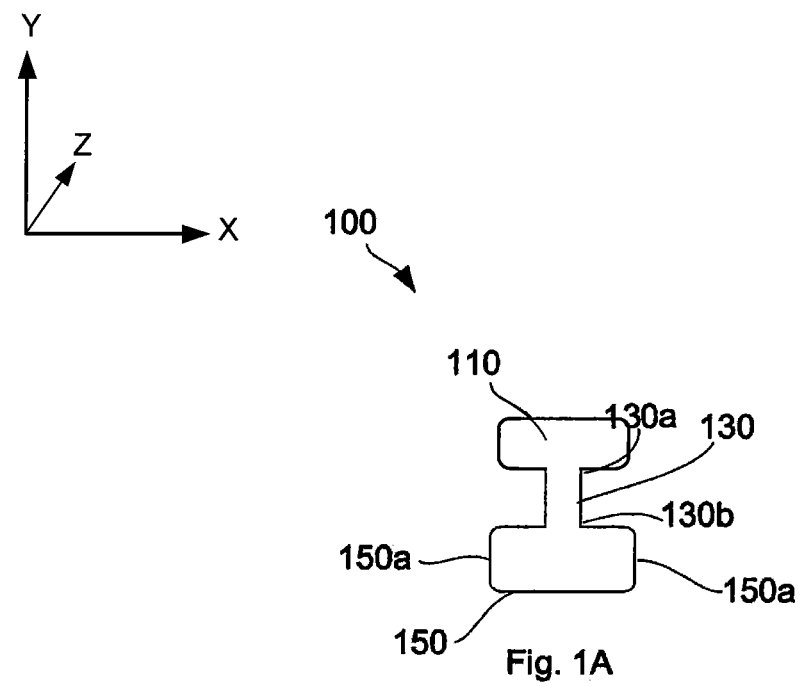
FIG. 1A is a top view of a nose clip in an unfolded configuration.

FIG. 1A is a top view of a nose clip 100 in an unfolded configuration. The nose clip 100 includes an outer support member 110, a bridge 130 with a first end 130a connected to the outer support member 110, and an inner support member 150 connected to a second end 130b of the bridge 130. In some embodiments, the outer support member 110, bridge 130, and inner support member 150 may be generally rectangular.

The inner member 150 may be generally larger than the outer support member 110 and curved to provide maximal improvement in the nasal airway. For example, the length of the inner support member 150 along an x-axis may be between about 10 mm and 30 mm, and the length of the inner support member 150 along a y-axis may be between about 5 mm and 10 mm. The length of the outer support member 110 along an x-axis may be between about 10 mm and 30 mm, and the length of the outer support 110 member along a y-axis may be between about 5 mm and 10 mm.

The length of the bridge along an X axis may be between about 2 mm and 6 mm. The length of the bridge along a Y axis may be between about 20 mm and 40 mm. The thickness of the inner support member, bridge, and outer support member in a Z direction may be about 1 mm. The dimensions of the respective elements may be changed to suit a particular need.

The nose clip 100 may be made of a malleable material that is soft enough to bend by hand, but rigid enough so that when bent, the inner support provides a force against a lateral side wall of the nose sufficient enough to move the lateral side wall of the nose to open the nasal airway. Additionally, the curvature of the inner support member 150 acts to create an outward curvature of the lateral wall of the nose and open the airway. For example, the nose clip 100 may be made out of suitably thick aluminum, other metals, or an alloy. In some embodiments, the malleable material may be encased in plastic or rubber (e.g., silicone rubber) to improve securing the nose clip 100 to the nose and to provide comfort.

Figure 1B:
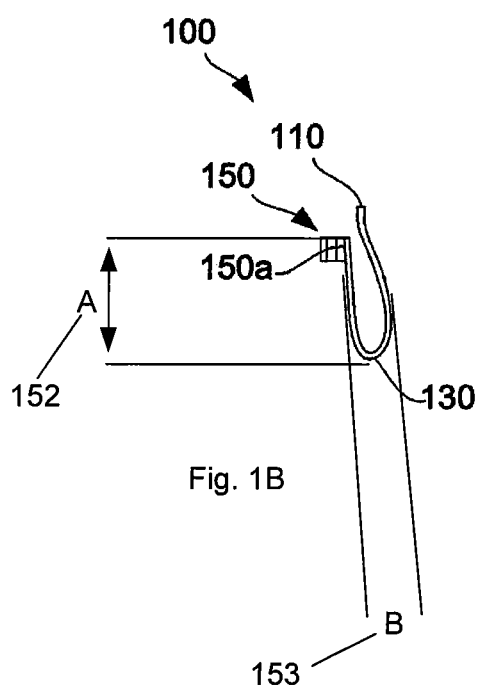
FIG. 1B is a side view of the nose clip showing a bent configuration of the nose clip.

The malleability of the nose clip 100 enables various configurations. For example, the nose clip 100 may be configured to be bent about the bridge 130, as shown in FIG. 1B. In this configuration, the nose clip 100 may be inserted into the nasal cavity as shown in FIG. 2D. For example, as shown in FIG. 2D the outer support member 110 may be configured to generally follow the contour of the outside surface 220 of a nose. The bridge 130 may be configured to generally follow the contour of the nose from the outside surface 200 near the outer support member, over the rim of the nostril 225, and into a surface in the nasal cavity 230. In this configuration, the distance A 152 (FIG. 1B) from the bridge portion that extends around the nostril margin to the end of the inner support member may be between about 10 mm and 30 mm. The angle B 153 (FIG. 1B) formed between the bridge portion in the nasal airway and the bridge portion outside the nose may be between about 0 and 5 degrees.

Figure 1C:
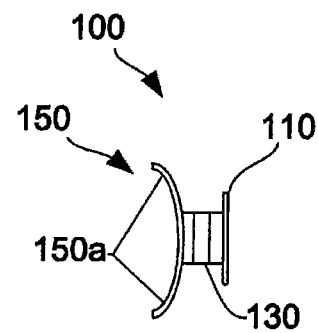
FIG. 1C is a top view of the nose clip that shows bent inner support member extensions.

Referring to FIG. 1C, inner support extensions 150a of the inner support member may also be bent. The inner support member 150 may be bent so that the inner support member extensions generally follow the contour of the inside surface of the nasal cavity and create an outward curvature of the lateral wall of the nose to open the airway. This enables creating a malleable character to the lateral nasal wall of the nose to allow shaping the lateral wall in an outward contour to enhance nasal airflow. This may enable evenly distributing the pressure exerted by the inner support member 150 against the inside surface of the nasal cavity. With the nose clip 100 bent appropriately, the nose clip 100 may be secured to a user's nose as shown in FIGS. 2A and 2C.

Figure 2A:
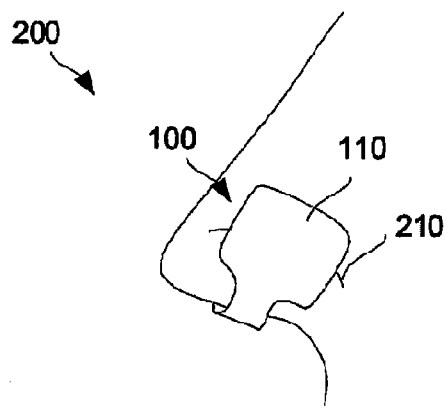
FIG. 2A is a side view illustration of an attached nose clip.

FIG. 2A is a side view illustration of the nose clip 100 mounted to the nose of a patient. As shown, the outer support member 110 is positioned adjacent to the nostril or the crease 210 that defines the nostril. However, the outer support member 110 may be positioned about a different region of the nose 200. For example, the outer support member 110 may be positioned higher up on the nose, towards the middle of the nose. The outer support member 110 may be made as large as the inner support member 150, thus creating more control over the lateral nasal wall contour.

Figure 2B:
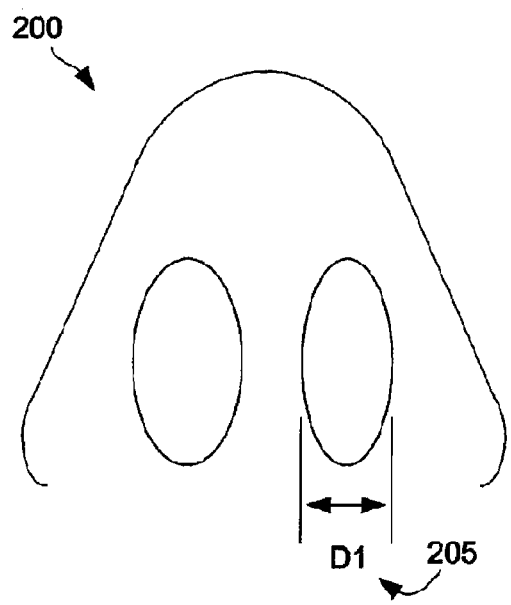
FIG. 2B is a bottom view illustration of a nose without a nose clip.
Figure 2C:
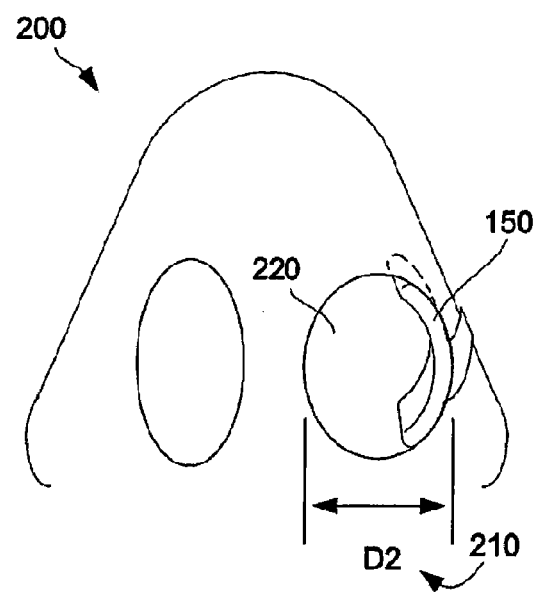
FIG. 2C is a bottom view illustration of the attached nose clip.
Figure 2D:
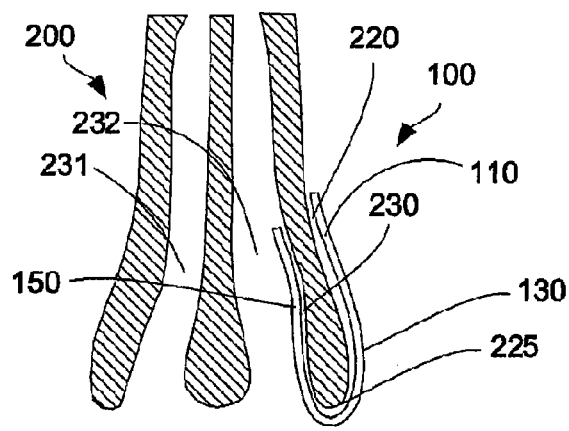
FIG. 2D is a cross-sectional view of a nose with an inserted nose clip.

FIG. 2B is a bottom view illustration of a nose showing collapse of the nasal airway. In this figure, the lateral width of the nasal airway is represented by reference D1 205. FIG. 2C is a bottom view illustration of the same nose with the attached nose clip 100. As shown, the inner support member 150 is inserted into the nasal cavity 220. The inner support member 150 may be positioned against a lateral sidewall of the nasal cavity. The contour of the inner support member 150 shapes the lateral sidewall in an outward contour to enhance nasal airflow. In one embodiment, the inner support member 150 is positioned near the nasal valve so that tension produced between the inner support member 150 and outer support member (not shown) move the lateral sidewall of the nasal cavity, thus improving airflow through the nasal cavity. The reshaping of the lateral sidewall and/or the tension produced between the inner support member 150 and the outer support member enable increased airflow through the nasal cavity. For example, the lateral width D2 210 of the nasal airway in FIG. 2C may be increased relative to the lateral width D1 205 of the nasal airway shown in FIG. 2B.

The inner support member 150 may be positioned elsewhere within the nasal cavity. For example, the inner support member 150 may be positioned in a region that is generally opposite to the crease that defines the nostril. The inner support member 150 may also be bent to create an outward contour to the lateral nasal wall to open the airway.

FIG. 2D is a cross-sectional view of a nose 200 with an inserted nose clip 100. As shown, the left (patient right) nasal airway 231 is smaller than the right (patient left) nasal airway 232. The right nasal airway 232 is increased by virtue of the pressure applied on the lateral sidewall of the right nasal airway 232 by the inner support member 150. In other words, the outer support member 110, bridge 130, and inner support member 150 work cooperatively to open the right nasal airway 232.

Figure 3:
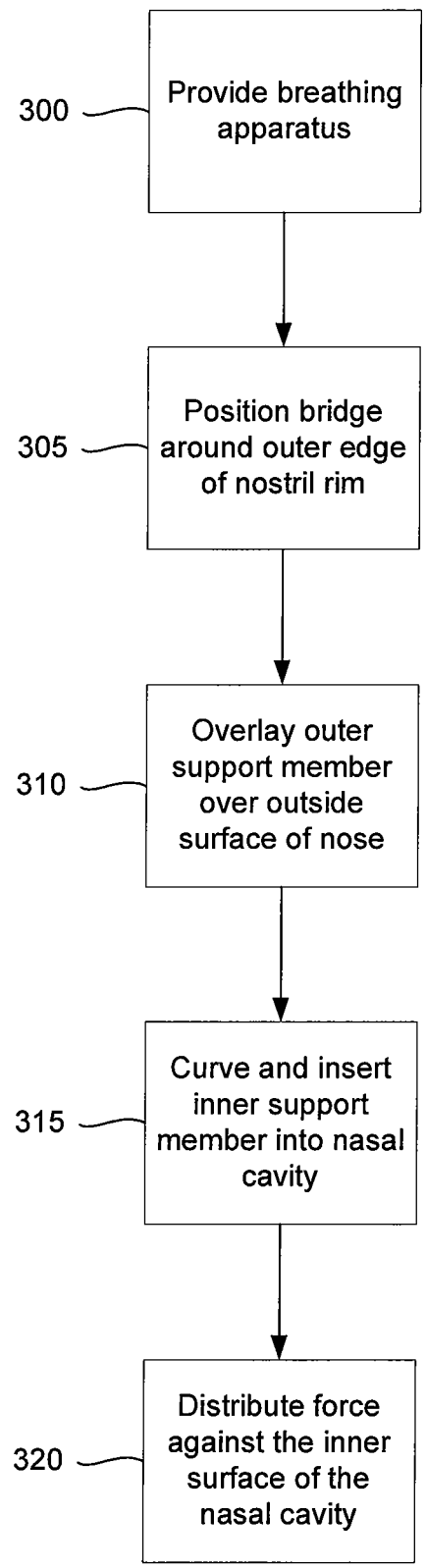
FIG. 3 is a flow diagram illustrating one methodology of using the nose clip of FIG. 1.

FIG. 3 is a flow diagram illustrating one methodology of using the nose clip 100 of FIG. 1. At block 300, a nose clip, such as the nose clip 100 of FIG. 1, may be provided.

At block 305, the bridge member may be positioned around an outer edge portion of a rim of a nostril. For example, the nose clip may be bent as shown in FIG. 1B.

At block 310, the outer support member may be overlaid over an outside surface of the nose. For example, the outer support member may be overlaid as shown in FIGS. 2A and 2D.

At block 315, the inner support member may be curved to follow the contour of the inner surface of the nasal cavity. Then the inner support member may be inserted into the nasal cavity. For example, the inner support member may be inserted as shown in FIGS. 2C and 2D.

At block 320, force applied by the inner support member against the nasal cavity may be distributed within the nasal cavity. For example, Inner support member extensions may be bent so that the inner support member biases the nasal wall to create an outward curvature of the lateral nasal wall and opens the nasal cavity. For example, the inner support member extensions may be bent as shown in FIG. 1C.

Once inserted, tension between the inner support member and outer support member forces a lateral movement of the lateral wall of the nasal cavity, thus opening the nasal airway and making it easier to breathe.

At block 320, the nose clip may be bent around the bridge to further refine the level of pressure applied against the lateral sidewall of the nasal cavity.

While the nose clip and method for using the nose clip have been described with reference to certain embodiments, it will be understood by those skilled in the art that various changes may be made and equivalents may be substituted without departing from the scope. For example, the overall width and length of the nose clip may be adapted to fit noses of different sizes. Moreover, the general shape of the nose clip may be changed. For example, the outer support member may have a circular shape, oval shape, or other shape. In some embodiments, the outer support member may be a loop of material with an opening in the center, such as a wire.

Figure 4A:
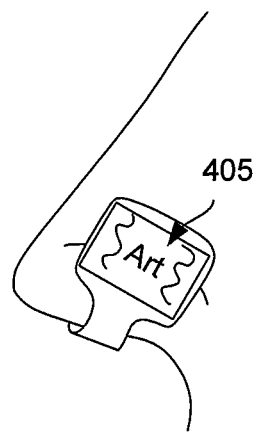
FIG. 4A illustrates a nose clip with artwork printed on an outer support member of the nose clip.
Figure 4B:
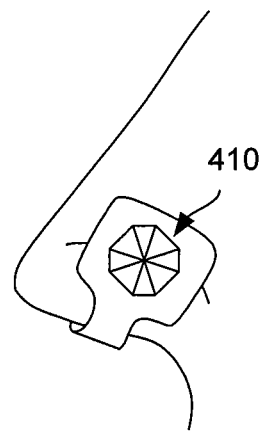
FIG. 4B illustrates a nose clip with jewelry on the outer support member of the nose clip.

In yet other embodiments, the outer support member may be adapted to hold a logo or artwork 405, as shown in FIG. 4A. For example, the logo of a manufacturer may be printed on a side of the outer support member. Alternatively, jewelry 410 may be placed on the outer support member to improve the aesthetics of the nose clip, as shown in FIG. 4B. The jewelry 410 may be fastened to the outer support member using various techniques known to those skilled in the art. For example, an adhesive may utilized to secure the jewelry to the outer support member.

The nose clip may also be made out of a more rigid material, such as steel. In some cases, the nose clip may be bent into a suitable configuration, such as the configuration shown in FIG. 1B, during a manufacturing process so that a user may simply insert the nose clip into the nasal cavity without any additional bending.

Figure 5A:
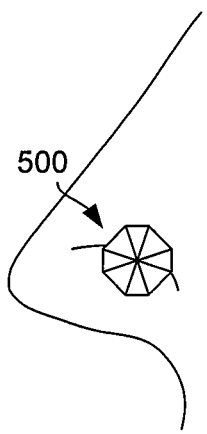
FIG. 5A illustrates a second embodiment of a nose clip.
Figures 5B, 5C:
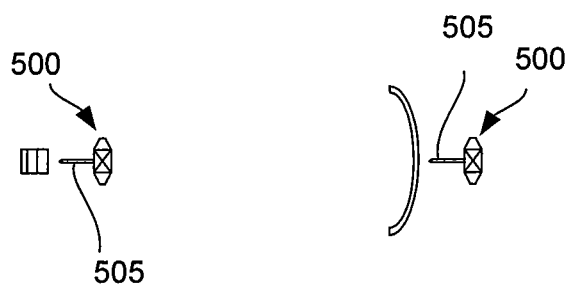
FIG. 5B is a side view of the second embodiment of the nose clip.
FIG. 5C is a top view of the second embodiment of the nose clip.

In other embodiments, a bridge may not be utilized. Rather, as shown in FIGS. 5A, 5B, and 5C, a pin 505 adapted to pierce the outer wall of the nose may be attached to the outer support member 500. The pin 505 may engage an inner support member adapted to receive the pin. The inner support member may include the features described above. Jewelry may be attached to the outer support member to enhance the aesthetic appearance of the nose clip.

In addition to these modifications, many other modifications may be made to adapt a particular situation or material to the teachings without departing from the scope of the claims. For example, the embodiments above may be modified to form a drug-delivery apparatus, as shown in FIGS. 7 and 8 and described below.

FIGS. 6A and 6B are front and back views, respectively, of an alternative nose clip 600 implementation. The nose clip 600 comprises a wire that defines an outer loop 605 and an inner loop 610. The wire may comprise spring properties and may be made of a material that comprises metal, plastic, rubber, a different material, or any combination of these materials. The wire may be closed so that there are no ends, as shown. Alternatively, the wire may be open at an end.

The outer loop 605 and inner loop 610 define a generally u-shaped lower end 618 as shown in FIG. 6C. The u-shaped lower end is configured to wrap under the rim of a nostril as shown in FIG. 6E. The u-shape may prevent pinching of the rim of the nostril when the nose clip 600 is in an attached configuration.

In a non-attached configuration, the outer loop 605 and inner loop 610 each define a plane. In some implementations, the planes defined by the outer 605 loop and inner loop 610 are in the same plane. For example, when the nose clip is not in use, the inner loop 610 may be disposed in the plane defined by the outer loop 605. In other words, the inner loop may be disposed generally inside of the inner loop when viewed from both the front and side. In other implementations, an angle is formed between the planes to increase the spring force produced between the inner loop 610 and the outer loop 605 when the nose clip 600. For example, in an unattached configuration, the inner loop 610 may go through the outer loop. In yet another implementation, the inner loop 610 is distanced away from the outer loop 605, as shown in FIG. 6C. The amount of pressure applied by the nose clip may be controlled by changing the relative distance between the outer loop 605 and the inner loop 610.

The outer loop 605 is configured to be placed on the outside surface of the nose in the area around a nostril, as shown in FIG. 6C. The width W1 615 of the outer loop 605 at the widest region of the outer loop 605 may be sized so that the outer loop 605 extends around the nostril. For example, the width W1 615 may be between about 10 mm and 25 mm. The height H1 620 of the outer loop 605 from the apex 625 of the outer loop 605 to the bottom 630 of the nose clip 600 may be sized so that the top region 635 of the outer loop 605 extends completely over the nostril when the nose clip 600 is in the attached configuration The inner loop 610 is configured to be placed on the inside surface of the nostril on the surface opposite to the outer surface of the nose upon which the outer loop 605 is positioned, as shown in FIG. 6D. The width W2 640 of the inner loop 610 is smaller than the width of the outer loop 605 and may be sized to distribute the spring force and/or to provide comfort. For example, the width W2 640 of the inner loop 610 at the widest region of the inner loop 610 may be between about 5 mm and 15 mm. The apex 645 of the inner loop 610 may be distanced from the apex 625 of the outer loop 605 by a distance D1 650 of about 5 mm to 15 mm, as shown in FIG. 6A.

In an attached configuration, the nose clip 600 is secured to the lower portion of the nose by positioning the outer loop 600 outside of the nose and the inner loop 610 inside the nasal airway, as shown in FIG. 6C and FIG. 6D. The outer loop 605 and the inner loop 610 work cooperatively so that the spring force between the inner loop 610 and outer loop 605 forces the inner surface of the nasal airway in contact with the inner loop 610 to move laterally towards the plane defined by the outer loop 605, thus increasing airflow through the nasal airway.

In some implementations, the nose clip may be configured to receive artwork (not shown), such as a logo. For example, a logo may be printed on a sheet that is configured to span the outer loop. The outer loop and/or sheet may include an adhesive for securing the sheet to the outer loop. Alternatively, the artwork may be slid over the outer loop. For example, the artwork may be printed on one of two sheets joined on three edges and open on a fourth edge. The open edge may be slid over the outer loop before the nose clip is attached.

Figures 7A, 7B:
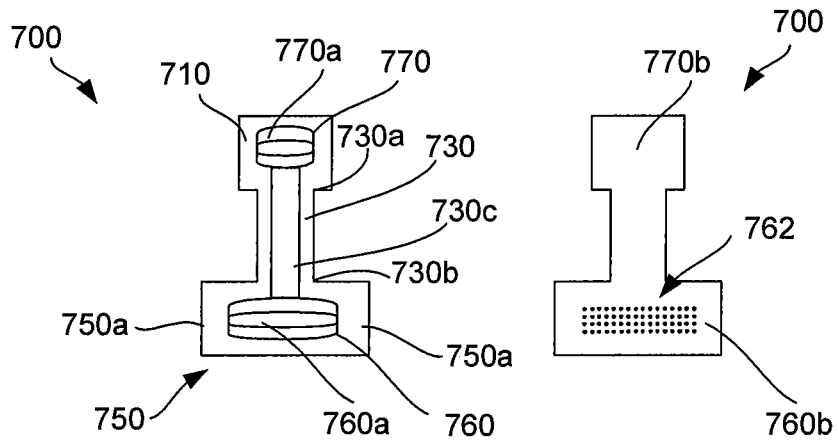
FIG. 7A illustrates a top side view of a drug delivery apparatus.
FIG. 7B illustrates a bottom side view of the drug delivery apparatus of FIG. 4A.
Figure 8:
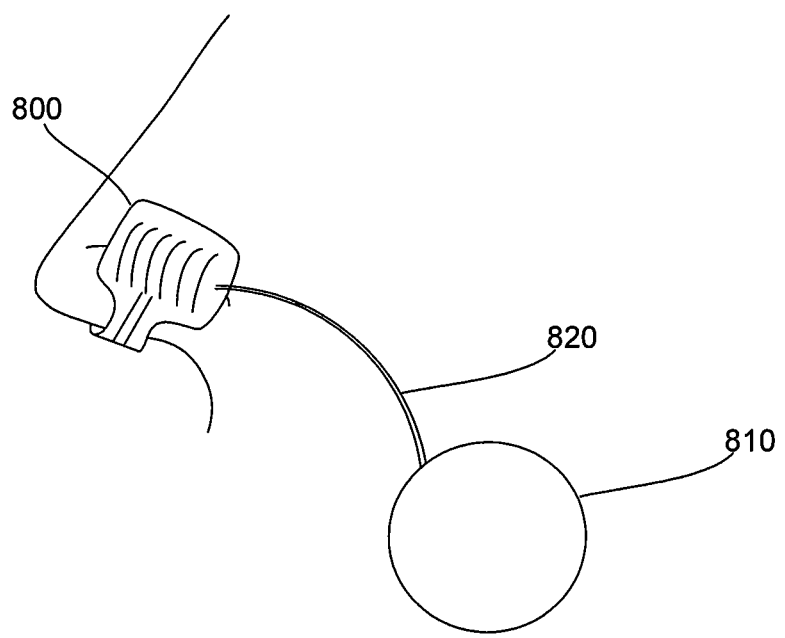
FIG. 8 shows another embodiment of a drug-dispensing apparatus in an attached configuration.

FIG. 7A illustrates a top side view of a drug-delivery apparatus 700, and FIG. 7B illustrates a bottom side view of the drug-delivery apparatus 700. The drug-delivery apparatus 700 includes an outer support member 710, a bridge 730 connected at a first end 730a to the outer support member 710, and a drug-dispensing portion 750 connected to a second end 730b of the bridge 730.

The drug-dispensing portion 750 may include inner support extensions 750a that extend away from the center of the drug-dispensing portion 750. The inner support extensions 750a may provide similar advantages to the inner support extensions of the nose clip 100 described above.

The drug-dispensing portion 750 may be adapted to deliver drugs to a patient via the nasal airway. For example, a top surface 760a and a bottom surface 760b of the drug-dispensing portion 750 may define a hollow region 760 in between the respective surfaces for storing and/or dispensing drugs. As shown in FIG. 7B, a porous surface 762 may be provided on the bottom surface of the drug-dispensing apparatus 700 to allow for delivery of the drug. The porous surface 762 may correspond to a series of perforations. Alternatively, the porous surface 702 may comprise a sponge-like material or atomizing surface.

In some embodiments, the drug is delivered via an evaporation process that occurs when air passes over the porous surface 762. For example, the drug may be delivered to the intranasal mucosa (not shown) as the evaporation of the fluid containing the drug is carried onto the intranasal mucosa. The intranasal mucosa has the unique ability to absorb fluids and compounds into the bloodstream. Depending on the drug's dynamics, delivery and absorption characteristics, different pore sizes and surface areas on the drug-dispensing portion 750 may be used to control actual drug dosage. Drugs that can be delivered include, for example, medications for the treatment of diabetes, allergic rhinitis, pain control, snoring, and sleep apnea. For a patient with snoring or sleep apnea, humidification may be helpful; and the combination of improved nasal breathing and lubricants can help to minimize snoring and obstruction. Patients with a dry nose disorder known as atrophic rhinitis will find relief from humidification of their nasal airway if they are unable to do so due to surgery, radiation or other trauma.

In some embodiments, a top surface 770a and a bottom surface 770b of the outer support member 710 may define a hollow region 770 for storing drugs. The bridge 730 may include a channel 730c for fluidly communicating drugs stored in the outer support member 710 to the drug-dispensing portion 750. This enables increased drug-storage capacity of the drug-dispensing apparatus 700. In some embodiments, the drug may be stored primarily in the outer support member 710 and/or channel 730c of the bridge 730 rather than the drug-dispensing portion 750. This enables the drug-dispensing portion 750 to be sized smaller to comfortably fit within the nasal cavity.

In some embodiments, drugs may be added to the drug-delivery apparatus by injecting the drugs into an injection receptacle or port (not shown) on the outer support member 710 of the drug-delivery apparatus 700. Alternatively, a separate drug capsule may be attached to the drug-delivery apparatus 700. Additionally, the drugs may be prepackaged in the drug-delivery apparatus 700 so that no manipulation of the drug-delivery apparatus 700 is necessary.

In addition to drugs, different scents may be placed into the drug-delivery apparatus 700. For example, those who would like to create scents for their nose may place different scents into the drug-delivery apparatus 700 and then deliver multiple different scents into their nose. This may be used to overcome unpleasant odors from the nose and sinuses or simply to enjoy one of a number of pleasant scents while one breathes through the nose.

Figure 7C:
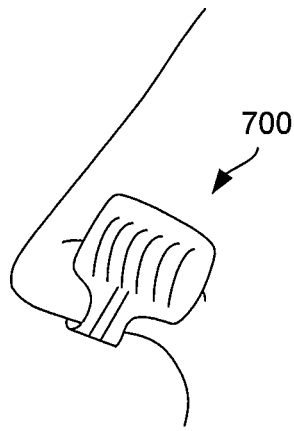
FIGS. 7C and 7D are side and bottom views, respectively, of the drug dispensing apparatus of FIG. 4A in an attached configuration.
Figure 7D:
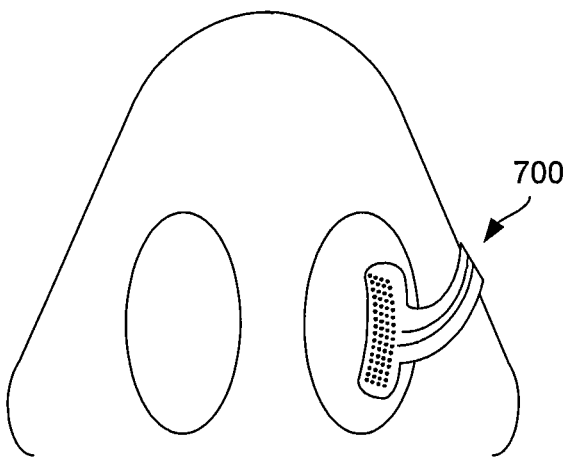

FIGS. 7C and 7D illustrate the drug-dispensing apparatus 700 in an attached configuration. The drug-dispensing apparatus 700 may be attached to a patient's nose in the same way as the nose clip described above may be attached to a user's nose. For example, the drug-dispensing apparatus 700 may be bent about the bridge and then inserted into the nasal cavity. To further secure the drug-dispensing apparatus, the bridge may be bent further to achieve the desired amount of pressure.

FIG. 8 shows yet another embodiment of a drug-dispensing apparatus 800 in an attached configuration. As shown, a bulb 810 may be connected to the drug-dispensing apparatus 800 via tubing 820. The bulb 810 may be utilized to store larger amounts of drugs or other substances. For example, the bulb 810 may be used to deliver humidification to the nasal cavity. Patients with a dry nasal cavity, symptoms consistent with atrophic rhinitis, or those who have lost the ability to humidify airflow can be treated by placing water in the bulb 810 and allowing water to travel into the drug-dispensing portion so that water can evaporate and humidify nasal airflow. The patients can wear the bulb 810 on their clothing fastened with a safety pin or placed in their pocket. The bulb 810 can be filled with water and allowed to hydrate the nasal cavity throughout the night or day. With the drug-dispensing apparatus 800 placed on both nasal sidewalls, a significant amount of hydration can be delivered to the nasal cavity.

The bulb 810 may also be utilized to deliver medications in an aqueous solution to the mucosa of the nasal cavity via the drug-dispensing apparatus. This may enable treating, for example, diabetes, allergic rhinitis, and for providing pain management. Antiviral or similar agents may also be delivered to the nasal mucosa to decrease the likelihood of contracting viral infections or other infectious diseases.

While the drug-delivery apparatus and method for using the drug-delivery apparatus have been described with reference to certain embodiments, it will be understood by those skilled in the art that various changes may be made and equivalents may be substituted without departing from the scope. Therefore, it is intended that the present apparatus and method of using the apparatus not be limited to the particular embodiment disclosed, but that the method and system include all embodiments falling within the scope of the appended claims.

I claim:

1. A device for improving airflow through a human nasal cavity, the device comprising:
    an outer support member configured to overlay a contour of an outside surface of a human nose at a first region that is at or above a crease that defines a nostril;
    a pair of inner support member extensions that extend from a central section in generally opposite directions, wherein the inner support member extensions are configured to press against an outer lateral sidewall of the nasal cavity at a second region that is below the first region, to maintain the second region of the nose below the first region and distribute a force against the outer lateral sidewall to shape a contour of the outer lateral sidewall of the nasal cavity of the nose, wherein the inner support member extensions together have a cross-section that defines a segment of a path that follows an inner circumference of the nasal cavity that is defined between the outer lateral sidewall and the nasal septum, wherein an open section between respective ends of the inner support member extensions span a section of the path that runs along the nasal septum to thereby minimize contact between the inner support member and the nasal septum and a top end of the outer support member is positioned above a top of the inner support member;
    a bridge member connected at one end to the outer support member and at a second end to the central section between the respective ends of the pair of inner support member extensions, wherein the bridge member is configured to be positioned around an outer edge portion of a rim of a nostril, and the outer support member, inner support member and bridge member configured to cooperate to increase a width of the nasal cavity to allow more air to flow through the nasal cavity,
    wherein a top edge of the inner support member is disposed below the first region and wherein the device is formed from a malleable material.

2. The device according to claim 1, wherein the bridge member is made of a malleable material.

3. The device according to claim 1, wherein the inner support member extensions are made of a malleable material.

4. The device according to claim 1, wherein the outer support member, bridge, and inner support member are made of a malleable material surrounded by a plastic material.

5. The device according to claim 1, wherein the outer support member is defined by a loop that is open in a center region.

6. The device according to claim 1, wherein the outer support member, bridge, and inner support member are sized to fit different size noses.

7. The device according to claim 1, further comprising a logo printed on the outer support member.

8. The device according to claim 1, wherein a first surface of the inner support member that faces the outer lateral sidewall of the nasal cavity and a second surface of the inner support member that faces an interior passage of the nasal cavity define a hollow region therebetween that is configured to store a drug, wherein the second surface of the inner support member is perforated to facilitate dispensing of the drug into the nasal cavity.

9. The device according to claim 1, further comprising a hollow region defined between a first and a second surfaces on the outer support member for storage of drugs.

10. The device according to claim 9, further comprising a channel defined in the bridge that allows for fluid communication of drugs stored in the hollow region of the outer support member to the hollow region of the inner support member.

11. The device according to claim 8, further comprising a bulb and tubing that allows for fluid communication of drugs stored in the bulb to the hollow region defined within the inner support member.

12. The device according to claim 1, further comprising support member extensions extending from the hollow region of the inner support member configured to follow a contour of the inner surface of the nasal cavity.

13. A method for improving airflow in the nasal airway, the method comprising:
provid ing a nose clip device according to claim 1;
positioning the bridge member of the nose clip around the outer edge portion of the rim of the nostril;
positioning the outer support member of the nose clip against the outside surface of the nose; and
positioning the inner support member of the nose clip against the lateral sidewall of the nasal cavity, the inner support member being configured to reshape the lateral sidewall of the nasal cavity, wherein spring force between the inner support member and the outer support member operates to increase the width of the nasal cavity so that airflow through the nasal cavity is increased.

14. The method according to claim 13, further comprising bending inner support member extensions extending from the inner support member so that the inner support member extensions create a contour of the inner surface of the nostril that is convex and bent outwardly.

15. The method according to claim 13, further comprising printing artwork on the outer support member.

16. The method according to claim 13, further comprising defining a hollow region between first and second surfaces of the inner support member for storage of drugs, at least one of the first and second surfaces includes one or more perforations for dispensing drugs into a nasal airway.

17. The method according to claim 16, further comprising communicating drugs from a bulb to the inner support member via a tube.

18. A device for improving airflow through a human nasal cavity, the device comprising:
a superior outer support member configured to overlay a contour of an outside surface of a nose at a first region;
a bridge member with a first end connected to the outer support member, the bridge member is configured to be wrapped around an outer edge portion of a rim of a nostril;
an inner support member comprising a pair of inner support member extensions that extend from a central section in generally opposite directions, the inner support member being inferior to the outer support member connected to a second end of the bridge member, wherein a major axis of the inner support member extends in a generally perpendicular direction with respect to the bridge member and is configured to press against an outer lateral sidewall of the nasal cavity at a second region that is below the first region to distribute a force against the outer lateral sidewall to shape a contour of the outer lateral sidewall of the nasal cavity of the nose, wherein a cross-section of the inner support member has a shape that follows an arc segment of a path that follows an inner circumference of the nasal cavity that is defined between the outer lateral sidewall and the nasal septum, wherein an open section between respective ends of the inner support member is configured to be adjacent to the nasal septum to thereby minimize contact between the inner support member and the nasal septum,
wherein the outer support member, inner support member and bridge member configured to cooperate to increase a width of the nasal cavity to allow more air to flow through the nasal cavity, and wherein the device is formed from a malleable material.

19. The device according to claim 1, wherein a major axis that runs between respective ends of the pair of the inner support members and the central section extends in a generally perpendicular direction with respect to the bridge member.

20. The device according to claim 1, wherein the inner support member does not contact the nasal septum when inserted into the nasal cavity to shape the contour of the outer lateral sidewall of the nasal cavity.

21. The device according to claim 18, wherein the inner support member does not contact the nasal septum when inserted into the nasal cavity to shape the contour of the outer lateral sidewall of the nasal cavity.

22. The device according to claim 19, wherein a length of the major axis is between about 10 mm and 30 mm and a width of the bridge member, taken in a same direction as the major axis between the respective ends of the pair of the inner support members, is between about 2 mm and 6 mm.

* * * * *